United States Patent [19]

Cooke et al.

[11] 4,021,230
[45] May 3, 1977

[54] METHOD FOR PROTECTING PLANT LIFE FROM INJURY DUE TO FROST OR SUB-FREEZING TEMEPRATURES

[75] Inventors: Anson Richard Cooke, Hatfield; John Whitney Long, Chalfont, both of Pa.; Steven John Wiedman, Morton, Ill.

[73] Assignee: Amchem Products, Inc., Ambler, Pa.

[22] Filed: Oct. 20, 1975

[21] Appl. No.: 623,883

[52] U.S. Cl. .................. 71/111; 71/86; 71/103; 71/118; 47/57.6
[51] Int. Cl.² .............. A01N 9/20; A01N 9/14
[58] Field of Search ............ 71/106, 111, 118, 86, 71/103

[56] References Cited

UNITED STATES PATENTS

| | | | |
|---|---|---|---|
| 3,428,678 | 2/1969 | Trepanier | 71/118 X |
| 3,485,806 | 12/1969 | Bloomquist et al. | 71/85 X |
| 3,867,126 | 2/1975 | Kupelian | 71/92 |
| 3,926,613 | 12/1975 | Alt | 71/118 |

Primary Examiner—Joseph Paul Brust
Attorney, Agent, or Firm—Ernest G. Szoke; Michael E. Zall; Ruth S. Moyerman

[57] ABSTRACT

A method of protecting plant life from injury due to frost or sub-freezing temperatures which comprises applying to the plant an effective, but non-phytotoxic amount, having regard to the plant being treated of a compound of the formula:

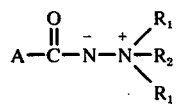

wherein $R_1$ is lower-alkyl;
$R_2$ is selected from the group consisting of:
  a. lower-alkyl, and
  b. 2-hydroxy alkyl of 3 to 18 carbon atoms; and -
A is selected from the group consisting of:
  a. alkyl of 3 to 13 carbon atoms,
  b. 2-hydroxy-lower alkyl,
  c. lower alkenyl,
  d. substituted phenyl, substituted by substituents selected from the group consisting of:
    i. p-nitro,
    ii. halo, and
    iii. lower alkoxy, (e)

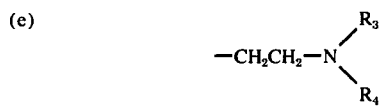

wherein
$R_3$ and $R_4$ are each independently selected from the group consisting of:
  i. hydrogen,
  ii. alkyl of 2 to 18 carbon atoms,
  iii. substituted phenyl,
  iv. benzyl,
  v. lower-alkoxy carbonyl, and
  vi. 2-hydroxy-lower alkyl; and (f)

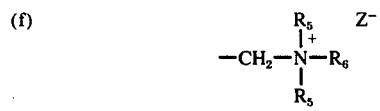

wherein
$R_5$ is lower alkyl;
$R_6$ is selected from the group consisting of:
  i. alkyl of 3 to 8 carbon atoms,
  ii. 2-hydroxy lower alkyl, and
$Z^-$ is an agriculturally acceptable anion.

63 Claims, No Drawings

METHOD FOR PROTECTING PLANT LIFE FROM INJURY DUE TO FROST OR SUB-FREEZING TEMEPRATURES

BACKGROUND OF THE INVENTION

This invention relates to a method of regulating the growth of plants, principally to a method of protecting plant life from injury due to frost or sub-freezing temperatures using various ammonium imines.

It is common knowledge that frost and sub-freezing temperatures can have serious, and sometimes permanent injurious effects on plants. This is, of course, particularly important in crop production, and each year there are tremendous losses in both vegetable and fruit production due to frost damage. For example, frost may have a particularly severe effect on peach production; entire crops of growing peaches have been eliminated by frost or freezing conditions. Other fruit crops that are particularly susceptible to frost include apples, strawberries and pears.

However, it is not only fruit crops that are damaged by frost; vegetable and cereal crops may suffer in the same way. Sugar beets and tomatoes are examples of vegetable crops which are particularly susceptible to damage at freezing and sub-freezing temperatures.

The damage caused by frost and sub-freezing temperatures does not always result in the killing of crops and plants, and often results in only a partial injury thereto. This injury can, however, have serious consequences, particularly in horticultural and agronomic crops. For example, a late spring frost can cause lopsided fruit and russeting in apple crops, while corn subjected to frost in its early stages of development, may also be severly injured.

At present there is little effective protection that can be afforded to plants on a commercial scale. Simple and inexpensive methods of protection have been sought for some time.

The simplest, mechanical means of protection that have been used in the past involved covering the plants with a layer of insulation. This insulating layer can be a sheet of material such as paper or plastics. However, this method is of very limited effectiveness, and is clearly impractical for large areas of crops, or indeed individual crops of large size - such as fruit trees.

Other insulating layers that have been used, particularly to protect fruit trees, include smoke, fogs and foams. Again these methods have a very limited use and effectiveness, and fogs and smoke are clearly impractible if it is windy. Moreover, in recent years the use of smoke for such purposes has become unacceptable because of resulting air pollution.

A number of chemical methods have also been tried over the years, and the following list contains examples of such methods:

U.S. Pat. No. 2,185,663 utilizes an emulsion of petroleum oil and water carrying a simple alcohol;

U.S. Pat. No. 2,610,117 utilizes a plant hormone mixed with a substance having anti-pellagric activity and a substance having vitamin K activity;

U.S. Pat. No. 3,045,394 utilizes a polymer of N-vinyl-2-pyrrolidone in a non-phytotoxic carrier;

U.S. Pat. No. 3,120,445 utilizes a mixture of hydrated lime, bentonite clay, and water;

U.S. Pat. No. 3,129,529 utilizes a coating of an emulsion of wax dissolved in an organic solvent of petroleum hydrocarbons and a surface active agent;

U.S. Pat. No. 3,555,727 utilizes aqueous sugar beet molasses;

U.S. Pat. No. 3,578,679 describes the use of N,N-dimethyldecenylsuccinamic acid; N-dimethylamino-decenyl-succinamic acid; and N-dimethylamino-decenylsuccinimide; and U.S. Pat. No. 3,867,126 describes the use of 3,6-dioxo-4-pyridazine acetic acid derivatives.

However, to date these methods have not provided an entirely satisfactory solution to the problem of protecting plant life from frost.

SUMMARY OF THE INVENTION

Accordingly, this invention provides a method of protecting a plant from injury due to frost and sub-freezing temperatures, which comprises applying to the plant an effective, but non-phytotoxic amount, having regard to the plant being treated of a compound of the formula:

$$A-\overset{O}{\overset{\|}{C}}-N-\overset{-}{\underset{}{N}}\overset{+}{\underset{}{-}}\overset{R_1}{\underset{R_1}{\diagdown N-R_2}}$$

wherein
R$_1$ is lower-alkyl;
R$_2$ is selected from the group consisting of:
 a. lower-alkyl, and
 b. 2-hydroxy alkyl of 3 to 18 carbon atoms; and
A is selected from the group consisting of:
 a. alkyl of 3 to 13 carbon atoms,
 b. 2-hydroxy-lower alkyl,
 c. lower alkenyl,
 d. substituted phenyl, substituted by substituents selected from the group consisting of:
  i. p-nitro,
  ii. halo, and
  iii. lower alkoxy, (e)
$$-CH_2CH_2-N\diagdown\overset{R_3}{\underset{R_4}{}}$$

wherein
R$_3$ and R$_4$ are each independently selected from the group consisting of:
 i. hydrogen,
 ii. alkyl of 2 to 18 carbon atoms,
 iii. substituted phenyl,
 iv. benzyl,
 v. lower-alkoxy carbonyl, and
 vi. 2-hydroxy-lower alkyl, and (f)
$$-CH_2-\overset{R_5}{\underset{R_5}{\overset{|+}{N}}}-R_6\quad Z^-$$

wherein
R$_5$ is lower alkyl;
R$_6$ is selected from the group consisting of:
 i. alkyl of 3 to 8 carbon atoms,
 ii. 2-hydroxy lower alkyl, and
Z$^-$ is an agriculturally acceptable anion.

DETAILED DESCRIPTION OF THE INVENTION

By the term lower alkyl is meant a straight or branched chain saturated hydrocarbyl group having from 1 to 5 carbon atoms.

By the term alkyl of 3 to 13 carbon atoms, alkyl of 2 to 18 carbon atoms or alkyl of 3 to 8 carbon atoms is meant a straight or branched chain saturated hydrocarbyl group having the indicated numbers of carbon atoms.

By the term 2-hydroxy-lower alkyl is meant a lower alkyl (a straight or branched chain saturated hydrocarbyl group having from 2 to 5 carbon atoms) wherein a hydrogen atom on the 2-carbon atom is replaced by a hydroxyl group.

By the term 2-hydroxy-alkyl of 3 to 18 carbon atoms is meant a straight or branched chain saturated hydrocarbyl group having 3 to 18 carbon atoms, wherein a hydrogen atom on the 2-carbon atom is replaced by a hydroxyl group.

By the term lower alkenyl is meant a straight or branched chain hydrocarbyl having from 3 to 5 carbon atoms and at least one double bond.

By the term substituted phenyl is meant a substituent of the formula:

wherein
X is a substituent selected from the group consisting of:
 i. p-nitro
 ii. halo, and
 iii. lower alkoxy.

By the term halo as used herein is meant one of the familiar halogen radicals, namely fluorine, chlorine, bromine or iodine. A preferred halo substituent is chlorine.

By the term lower alkoxy is meant an alkoxy group R—O—, wherein R is a lower alkyl group. A preferred lower alkoxy substituent is methoxy.

By the term benzyl is meant a substituent of the formula:

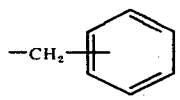

By the term lower-alkoxy carbonyl is meant a carbonyl group of the formula:

wherein R' is a lower alkoxy group.

By the term agriculturally acceptable anion is meant an anion which does not have any harmful or deleterious effect on the plant being treated when used in the method of this invention. There are a very large number of agriculturally acceptable anions, as would readily be appreciated by one skilled in the art. By way of illustration, it may be said that amongst this wide variety of suitable anions, particularly suitable anions are halide (particularly chloride), nitrite, nitrate, diacid phosphate, sulfate and alkylsulfate ions. Preferably, $Z^-$ is a chloride ion.

A highly preferred group of compounds is the group wherein $R_1$ is methyl.

Another highly preferred group of compounds is the group wherein $R_2$ is methyl.

A very highly preferred group of compounds is the group wherein $R_1$ and $R_2$ are both methyl.

When $R_2$ is 2-hydroxy alkyl of 3 to 18 carbon atoms it is preferred that the alkyl group be a straight chain alkyl group.

Particularly preferred 2-hydroxy-alkyl groups include 2-hydroxy-n-propyl, 2-hydroxy-n-octyl and 2-hydroxy-n-octadecyl.

A highly preferred group of compounds is the group of compounds wherein $R_1$ is methyl and $R_2$ is 2-hydroxy-propyl.

Several highly preferred groups of compounds are:

When A is alkyl of 3 to 13 carbon atoms it is particularly preferred that the group be the isopropyl and n-tridecyl alkyl groups When A is 2-hydroxy lower alkyl it is particularly preferred that the group be the 2-hydroxy ethyl group When A is lower alkenyl it is particularly preferred that the group be the 2-allyl group When A is substituted phenyl it is particularly preferred that the groups be the p-nitro, chloro and methoxy substituted phenyl groups, and in particular the o-chloro substituted phenyl group When A is:

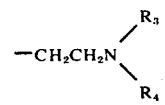

it is particularly preferred that when $R_3$ or $R_4$ is alkyl that it be a straight chain alkyl group. Particularly preferred alkyl groups are the ethyl, butyl, dodecyl, hexadecyl and octadecyl groups;

When $R_3$ or $R_4$ is 2-hydroxy alkyl of 3 to 18 carbon atoms, a preferred group is the 2-hydroxy-propyl group; and When $R_3$ or $R_4$ is lower alkoxy carbonyl, a preferred group is methoxycarbonyl When A is:

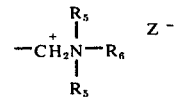

it is particularly preferred that when $R_5$ is lower alkyl that it be methyl;

When $R_6$ is alkyl a preferred group is the straight chain alkyl groups, in particular n-octyl; and When $R_6$ is 2-hydroxy lower alkyl, a particularly preferred group is 2-hydroxy ethyl.

Examples of ammonium imines which have been found to be of particular effectiveness in the method of this invention, and are therefore the preferred compounds for use in the invention, are:

(a) 1,1-dimethyl-1-(2-hydroxypropyl)-2-isobutyryl ammonium imine;

(b) 1,1-dimethyl-1-(2-hydroxypropyl)-2-tetradecanoyl ammonium imine;

(c) 1,1-dimethyl-1-(2-hydroxyoctadecyl)-2-(3-hydroxypropionyl) ammonium imine;

(d) 1,1-dimethyl-1-(2-hydroxyoctyl)-2-methacryloyl ammonium imine;

(e) 2-(4-nitrobenzoyl)-1,1,1-trimethyl ammonium imine;

(f) 2-(2-chlorobenzoyl)-1,1-dimethyl-1-(2-hydroxypropyl) ammonium imine;

(g) 1,1-dimethyl-1-(2-hydroxypropyl)-2-(4-methoxybenzoyl) ammonium imine;

(h) 1,1-dimethyl-1-(2-hydroxypropyl)-2-(3-octadecylaminopropionyl) ammonium imine;

(i) 1,1-dimethyl-1-(2-hydroxypropyl)-2- 3-{N-(2-hydroxypropyl)-N-octadecylamino]propionyl} ammonium imine;

(j) 2-[3-(3-chloroanilino)propionyl]-1,1-dimethyl-1-(2-hydroxypropyl) ammonium imine;

(k) 2-[(3-benzylamino)propionyl]-1,1-dimethyl-1-(2-hydroxypropyl) ammonium imine;

(l) 2-(3-diethylaminopropionyl)-1,1,1-trimethyl ammonium imine;

(m) 2-[3-(N-butyl-N-methoxycarbonylamino)propionyl]-1,1-dimethyl-1-(2-hydroxypropyl) ammonium imine;

(n) 1,1-dimethyl-2{3-[N-dodecyl-N-(2-hydroxylpropyl)amino]propionyl} 1-(2-hydroxypropyl) ammonium imine;

(o) 1,1-dimethyl-2-{3-[N-hexadecyl-N-(2-hydroxypropyl)amino]propionyl}-1-(2-hydroxypropyl) ammonium imine;

(p) 1,1-dimethyl-2-(2-dimethyl octylammonioacetyl)-1-(2-hydroxypropyl) ammonium imine chloride; and (q) 1,1-dimethyl-2-(dimethyl-2-hydroxyethyl ammonioacetyl)-1-(2-hydroxypropyl) ammonium imine chloride.

The most preferred ammonium imines for use in this invention are compound (n), 1,1-dimethyl-2-{3-[N-dodecyl-N-(2-hydroxypropyl)amino]propionyl}1-(2-hydroxypropyl) ammonium imine; and compound (f) 2-(2-chlorobenzoyl)-1,1-dimethyl-1-(2-hydroxypropyl) ammonium imine; the preferred rate of application for these compounds is 0.8 to 8.0 lbs/A.

The compounds used in the method of this invention can be easily prepared by one skilled in the art. The preparation of these compounds is described in detail in U.S. Pat. Nos. 3,485,806; 3,499,032; 3,527,802; and 3,706,800, the entire disclosures of which are incorporated herein by reference.

While it is possible that the compounds of the invention may be applied directly to the plant being treated in pure, undiluted form, it is normally more convenient to apply the compounds to the plant with a suitable vehicle in the form of a composition.

By the term suitable vehicle is meant any carrier or medium for containing the compound used in the invention in dissolved, dispersed, emulsified or otherwise suspended form, for transporting the compound being used in the method of the invention to the plant site being treated. The term suitable is intended to exclude any possibility that the vehicle, considered of course in relation to the means by which the composition is to be applied to the plant site, could be toxic to the plant being treated or have a harmful or undesirable effect upon the method of the invention.

Depending on how the composition is to be applied, the vehicle could be a solid (such as talc or vermiculite) or a liquid (such as water or a common organic solvent), and it is believed to be within the competence of those skilled in the art to choose the appropriate vehicle for particular applications.

It is frequently most convenient if the vehicle be, or contain, water and the compositions are preferably applied in the form of aqueous solution. Depending upon the solubility of the compound being used, it may be applied in aqueous solutions formed wholly or partially of water, or even as aqueous emulsions or dispersions. When an aqueous composition contains other solvents with the water these are usually common organic solvent. Preferred solvents include ketones such as acetone or methyl ethyl ketone and mono- and polyhydric alcohols such as propylene glycol and butoxy ethanol. If an ammonium imine is of particularly low solubility, it may be solubilized by the use of cosolvents and the like.

The method of the invention is not, of course, restricted to the application of a single ammonium imine to the plant under treatment, and extends to the application of two or more ammonium imines — whether applied separately or together in a single composition.

It will be well understood by any plant biologist that, as with any material used to treat plants, the compound of the invention should be applied to any particular plant at certain optimum application rates (either of concentration in solution, or of weight per unit of ground area) and at certain stages in the growth cycle of the plant, including the ungerminated seed, if they are to achieve the desired protection against frost and sub-freezing temperatures. These optimum application rates will be dictated by such things as the plant species being treated and the climatic conditions encountered. This makes it impossible to specify exact application rates for the compounds. However, such application rates can be determined readily for any particular case by standard procedures well known in themselves. For general guidance, experience indicates that the application rate will normally be chosen so as to apply from 0.05 to 50 pounds per acre of the ammonium imine, usually in fact within the narrower range from 0.1 to 10 pounds per acre, and most frequently within the still narrower range of from 0.25 to 5.0 pounds per acre.

When applied in the form of a solution, the compound of this invention will normally be present in concentrations of from 10 to 10,000 parts per million (thus from 0.001% to 1% by weight), and most often within the range of 100 to 5,000 parts per million, (thus from 0.01 to 0.5% by weight).

The compositions based on liquid carriers will normally have a water-thin consistency, and can then be applied with any form of conventional agricultural spraying or like equipment. Compositions based on solid carriers may be applied in the form of powder or granules by the appropriate conventional distribution equipment. Although the preferred method of application is directly to the foliage and stems of the plants, the plant-growth regulating compositions used in this invention may in some instances be applied to the medium in which the plants are growing, when they may be root-absorbed to a sufficient extent to yield the desired effect. Further, the plant growth regulating compositions may also, in some instances, be applied to the seed before planting.

While it is clear that, in applying the composition to standing crops and other vegetation, the significant factor is the quantity of the compound assimilated by the plants, it may be added that the indicated amounts of the ammonium imine may in general be applied in liquid formulations with a carrier comprising sufficient aqueous or other liquid diluent so that the total volume sprayed is from about 1 to 1,000 gallons per acre, but more usually from about 10 to 500 gallons per acre, depending on the method of application.

The compounds of this invention are most conveniently handled and stored in the form of a liquid concentrate, which may be diluted with the chosen carrier to form the composition for use in the method of this invention. Such concentrates may comprise solely the ammonium imine (that is, 100% active material) or may additionally comprise a liquid carrier in an amount such that the concentrate contains between 1 and 100% (by weight) of the compound. Preferably the active materials will be handled in the form of aqueous liquid concentrates (for dilution before use) in which the concentration of the compound is in the range of from 10 to 30% (by weight).

The compositions may with advantage incorporate surfactants, dispersing agents, emulsifiers, penetrants, sequestrants, stabilizers or combinations thereof. They may also — for specific purposes — incorporate plant growth regulators, herbicides, pesticides or combinations thereof.

It should be emphasized that the protection afforded by the method of this invention against frost and low temperature damage is applicable to a very wide variety of plants, including vegetables such as cucurbits, beans and sugar beets; grain and cereal crops such as corn, sorghum and wheat; fruit crops such as apples, cherries, grapes, pears, peaches and plums; horticultural flower crops such as petunias and marigolds; and nut crops such as pecans, filberts and walnuts. The protection extends to virtually every part of the plant under treatment, and thus may be used to protect the fruit, flowers, foliage or any other part of the plant.

Naturally plants should be treated by the method of this invention prior to the plants being subjected to the frost or sub-freezing temperatures. Plants treated according to the method of this invention have been found to show increased resistance to damage from frost and sub-freezing conditions over considerable periods of time. Improved frost protection has been observed after as short a time as 12–18 hours following treatment, while plants subjected to sub-freezing temperatures 4–5 days or even longer after treatment have also shown excellent resistance to frost and low temperature damage. There has even been indication of the method of this invention providing protection 2–3 weeks, or even longer, after treatment. This is of great advantage to the farmer as it means that if frost is forecast or seems imminent he may treat his crops according to the method of the invention and rapidly gain protection. At the same time the protection afforded to his crops will persist and protect them from damage for a considerable period of time, in the event of the frost or sub-freezing condtions persisting or being later than anticipated.

The following Evaluations are now given, though only by way of illustration, to show details of preferred compounds, methods, techniques and conditions employed in the treatment of plants to make them resistant to damage from frost and sub-freezing temperatures. By the terms freeze protection and frost protection as used herein is meant protection from injury or damage due to frost, freezing and sub-freezing temperatures.

EVALUATION 1

FREEZE PROTECTION OF ZUCCHINI SQUASH

Zucchini squash plants were treated with solutions containing the compounds being investigated when they were at the seedling stage. The solutions under test were applied either as a spray to the plants themselves or as a drench to the medium in which the plants were growing at the rates indicated in the table below. The treatments were replicated over a number of plants. To provide controls, a further set of plants were left untreated.

The treated and control plants were placed in a freezing chamber, where they were subjected to a 24 hour freezing cycle with a minimum temperature of 24° F and a total of 7 hours below 30° F.

After removal from the freezing chamber the treatments were assessed to determine the percentage survival for each treatment and for the controls. The results are expressed below in Table 1 as the percentage survival of the Zucchini squash plants for a variety of application rates and times between treatment and freezing.

In Table 1 the compounds are identified by letter — (a) to (q) — this lettering refers back to the list of preferred compounds set out hereinbefore. Unless indicated as having been applied as a drench, the compounds were applied as a spray.

TABLE 1

| Compound Applied | Formula | Time Between Treatment and Freezing (days) | Rate (lb/A) | Percentage Survival (%) Treated | Control |
|---|---|---|---|---|---|
| (a) | 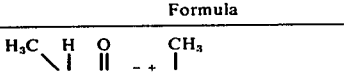 | 2<br>2<br>2 | 0.8<br>1.6<br>4.0 | 19<br>38<br>19 | 12<br>12<br>12 |
| (b) | 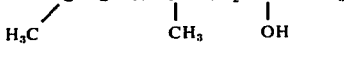 | 2<br>2<br>2 | 0.16<br>0.4<br>4.0 | 31<br>12<br>19 | 6<br>6<br>6 |
| (c) | 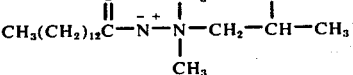 | 2 | 7.2 (drench) | 12 | 0 |

TABLE 1-continued

| Compound Applied | Formula | Time Between Treatment and Freezing (days) | Rate (lb/A) | Percentage Survival (%) Treated | Percentage Survival (%) Control |
|---|---|---|---|---|---|
| (d) | CH₂=C(CH₃)—C(O)—N⁻—N⁺(CH₃)₂—CH₂—CH(OH)—(CH₂)₅CH₃ | 2<br>2<br>2 | 0.16<br>0.4<br>1.6 | 56<br>50<br>44 | 31<br>31<br>31 |
| (e) | O₂N—C₆H₄—C(O)—N⁻—N⁺(CH₃)₃ | 2 | 7.2 (drench) | 19 | 0 |
| (f) | 2-Cl-C₆H₄—C(O)—N⁻—N⁺(CH₃)₂—CH₂CH(OH)CH₃ | 2<br>2 | 0.16<br>1.6 | 31<br>56 | 25<br>25 |
| (g) | H₃CO—C₆H₄—C(O)—N⁻—N⁺(CH₃)₂—CH₂CH(OH)CH₃ | 2 | 7.2 (drench) | 12 | 0 |
| (h) and | H₃₅C₁₈NH—CH₂—CH₂—C(O)—N⁻—N⁺(CH₃)₂—CH₂CH(OH)CH₃ | 2<br>2 | 1.6<br>4.0 | 12<br>44 | 6<br>6 |
| (i) Mixture | CH₃(CH₂)₁₇—N(CH₂CH(OH)CH₃)—CH₂—C(O)—N⁻—N⁺(CH₃)₂—CH₂CH(OH)CH₃ | 1 | 1.6 | 56 | |
| (j) | 3-Cl-C₆H₄—NH—CH₂—CH₂—C(O)—N⁻—N⁺(CH₃)₂—CH(OH)CH₃ | 2 | 7.2 (drench) | 31 | 0 |
| | | 4<br>4<br>4<br>2<br>2<br>2 | 0.8<br>1.6<br>3.2<br>0.16<br>0.4<br>0.4 | 19<br>12<br>25<br>25<br>25<br>31 | 6<br>6<br>6<br>12<br>12<br>6 |
| (k) | C₆H₅—CH₂—NH—CH₂CH₂—C(O)—N⁻—N⁺(CH₃)₂—CH₂CH(OH)CH₃ | 4<br>4<br>4 | .16<br>.40<br>.80 | 44<br>75<br>31 | 19<br>19<br>19 |
| (l) | (CH₃CH₂)₂N—CH₂—CH₂—C(O)—N⁻—N⁺(CH₃)₃ | 2 | 7.2 (drench) | 50 | 19 |
| | '' | 4<br>4<br>4<br>2<br>2<br>2<br>8 | 2.0<br>1.6<br>3.2<br>0.4<br>0.8<br>4.0<br>1.6 | 38<br>44<br>25<br>25<br>25<br>25<br>19 | 6<br>12<br>12<br>6<br>6<br>6<br>6 |
| (m) | CH₃(CH₂)₃—N(C(O)OCH₃)—CH₂CH₂—C(O)—N⁻—N⁺(CH₃)₂—CH₂CH(OH)CH₃ | 2 | 7.2 (drench) | 25 | 0 |
| | | 5<br>2 | 1.6<br>0.16 | 6<br>28 | 0<br>25 |

TABLE 1-continued

| Compound Applied | Formula | Time Between Treatment and Freezing (days) | Rate (lb/A) | Percentage Survival (%) Treated | Control |
|---|---|---|---|---|---|
| (n) | $H_{25}C_{12}-\underset{\underset{OH}{\overset{|}{CH_2CH-CH_3}}}{\overset{|}{N}}-CH_2-CH_2-\overset{O}{\overset{\|}{C}}-\overset{-}{N}\overset{+}{-}\underset{\overset{|}{CH_3}}{N}-\underset{\overset{|}{OH}}{CH_2CHCH_3}$ | 2 | 7.2 (drench) | 31 | 19 |
|  |  | 2 | 0.8 | 50 | 25 |
|  |  | 2 | 1.6 | 56 | 19 |
|  |  | 2 | 4.0 | 38 | 19 |
|  |  | 2 | 1.2 | 75 | 44 |
|  |  | 1 | 0.8 | 44 | 25 |
|  | + ethylene glycol (%) and glycerol (10%) |  |  |  |  |
| (o) | $CH_3(CH_2)_{15}-\underset{\underset{OH}{\overset{|}{CH_2-CH-CH_3}}}{\overset{|}{N}}-CH_2CH_2-\overset{O}{\overset{\|}{C}}-\overset{-}{N}\overset{+}{-}\underset{\overset{|}{CH_3}}{N}-CH_2-\underset{\overset{|}{OH}}{CH}-CH_3$ | 2 | 1.6 | 53 | 9 |
|  |  | 2 | 0.4 | 75 | 31 |
|  |  | 8 | 0.4 | 44 | 6 |
| (i) | $CH_3(CH_2)_{17}-\underset{\underset{OH}{\overset{|}{CH_2CHCH_3}}}{\overset{|}{N}}-CH_2CH_2-\overset{O}{\overset{\|}{C}}-\overset{-}{N}\overset{+}{-}\underset{\overset{|}{CH_3}}{N}-CH_2-\underset{\overset{|}{OH}}{CH}-CH_3$ | 2 | 0.16 | 12 | 0 |
|  |  | 2 | 0.4 | 12 | 0 |
|  |  | 2 | 0.8 | 19 | 0 |
|  |  | 2 | 1.6 | 6 | 0 |
|  |  | 4 | 0.4 | 31 | 12 |
| (p) | $CH_3(CH_2)_7-\underset{\overset{|}{CH_3}}{\overset{\overset{|}{CH_3}}{N}}-CH_2-\overset{O}{\overset{\|}{C}}-\overset{-}{N}\overset{+}{-}\underset{\overset{|}{CH_3}}{N}-\underset{\overset{|}{OH}}{CH_2CHCH_3}$ $Cl^-$ | 2 | 7.2 (drench) | 12 | 0 |
|  |  | 2 | 0.16 | 12 | 0 |
|  |  | 2 | 0.8 | 12 | 0 |
| (q) | $HOCH_2CH_2-\overset{+}{\underset{\overset{|}{CH_3Cl^-}}{\overset{\overset{|}{CH_3}}{N}}}-CH_2\overset{O}{\overset{\|}{C}}-\overset{-}{N}\overset{+}{-}\underset{\overset{|}{CH_3}}{N}-\underset{\overset{|}{OH}}{CH_2CHCH_3}$ | 2 | 7.2 (drench) | 12 |  |

These results show the effectiveness of the compounds of the invention in protecting the Zucchini squash plants from freeze injury. In many cases the untreated control plants were all killed, while a substantial proportion of the treated plants survived. The method of the invention would provide an extremely effective protection against the frost and freezing conditions encountered by crops.

Attention is drawn to the fact that in many instances the treated squash plants have a 200–500% better survival rate than the untreated plants.

EVALUATION 2

FREEZE PROTECTION OF GREAT NORTHERN BUSH BEAN

A similar test to that described in EVALUATION 1 was carried out on Great Northern Bush Bean plants. The plants were treated when they were seedlings by spraying with a solution of compound (n), i.e. 1,1-dimethyl-2{3[N-dodecyl-N-(2-hydroxypropyl)amino]-propionyl}1-(2-hydroxypropyl)ammonium imine. Each treatment was replicated over a number of plants.

1 day after treatment the treated and control plants were subjected to the freezing cycle as described in EVALUATION 1. The plants were then assessed to determine the percentage survival. The results are expressed in Table 2 below.

TABLE 2

| Application Rate (lb/A) | Percentage Survival (%) |
|---|---|
| 0.8 | 56 |
| Control (0) | 19 |

The results show that a considerable degree of protection was afforded to the bean plants by the method of the invention, as compared with the untreated control plants.

EVALUATION 3

FREEZE PROTECTION OF "CRANBERRY" BEANS

A similar test to that described in EVALUATION 2 was performed on bean plants of the Cranberry variety using compound (n). The solutions were sprayed onto the seedling plants at various rates, 2 days before the plants were subjected to the freezing cycle.

The results, expressed as percentage survival, are expressed in Table 3 below.

TABLE 3

| Application Rate (lb/A) | Percentage Survival (%) |
|---|---|
| 0.8 | 94 |
| 1.6 | 75 |

TABLE 3-continued

| Application Rate (lb/A) | Percentage Survival (%) |
|---|---|
| Control (0) | 56 |

It will be seen that bean plants of the Cranberry variety are generally more resistant to frost than the Great Northern Bush Bean; illustrated by the greater survival rate amongst the control plants. Nevertheless the treated plants showed a considerably greater degree of resistance to the freezing temperatures than the control plants, with nearly all surviving when treated at 0.8 lb/A, whereas less than 60% of the control plants survived.

EVALUATION 4
FREEZE PROTECTION OF CORN

A similar test to that described in EVALUATION 2 was performed on corn using compound (n).

The corn plants were treated when they were about 14 to 18 inches tall, and at the 4 to 5 leaf stage, by spraying a number of plants with solutions of compound (n).

The results, expressed as percentage survival, are given in Table 4 below.

TABLE 4

| Application Rate (lb/A) | Percentage Survival (%) |
|---|---|
| 0.16 | 12 |
| Control (0) | 0 |

Each application rate shows a substantial increase in survival of the corn plants as compared to the untreated, control plants, which all perished.

EVALUATION 5
FREEZE PROTECTION OF TOMATOES

A similar test to that described in Example 2 was performed on tomatoes using compound (n).

Rutgers tomato plants were treated when they were at the 5 leaf stage by spraying with a solution of compound (n). Eight (8) plants were treated in this manner.

The results, expressed as percentage survival are given in Table 5 below.

TABLE 5

| Application Rate (lb/A) | Percentage Survival (%) |
|---|---|
| 0.4 | 88 |
| Control (0) | 50 |

The treatment according to the method of the invention substantially increased the resistance of the tomato plants to sub-freezing temperatures.

EVALUATION 6
FREEZE PROTECTION OF PEACHES

A test was performed to determine the frost protection afforded to peach trees by the method of this invention.

Individual branches of growing peach trees were treated by spraying to run off with various concentrations of solutions of compound (n) at a time when the buds were at the green calyx and first bloom stages. Four (4) days after treatment the treated branches were removed and placed in plastic bags in a freezing chamber. The temperature of the chamber was reduced and branches removed at various temperatures.

Two (2) days after removal the branches were analyzed and the number of dead peach flower buds was determined.

The results are expressed in Table 6 below as percentage mortality for each solution concentration and freezing temperature.

TABLE 6

| Concentration Solution (ppm) | Percentage Mortality % | | |
|---|---|---|---|
| | 19° F | 16° F | 10° F |
| 500 | 2.8 | 6.3 | 14.3 |
| 200 | 3.9 | 6.4 | 7.0 |
| 0 (Control) | 8.6 | 28.8 | 43.5 |

These results show the considerable protection afforded to the peach blossom by treating with a compound used in the method of this invention.

A significant increase in survival is obtained even when the branches were subjected to temperatures as low as 10° F. At this extremely severe temperature the increase in survival was particularly marked, especially when the compound was applied at a concentration of 200 ppm.

We claim:

1. A method of protecting a plant from injury from frost and sub-freezing temperatures, which comprises applying to the plant an effective, but non-phytotoxic amount, having regard to the plant being treated, of a compound of the formula:

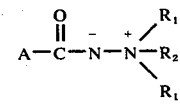

wherein
$R_1$ is lower-alkyl containing from one to five carbon atoms;
$R_2$ is selected from the group consisting of:
  a. lower-alkyl containing from one to five carbon atoms, and
  b. 2-hydroxy alkyl of 3 to 18 carbon atoms; and
A is selected from the group consisting of:
  a. alkyl of 3 to 13 carbon atoms,
  b. 2-hydroxy-lower alkyl containing from one to five carbon atoms,
  c. lower alkenyl containing from three to five carbon atoms and one double bond,
  d. substituted phenyl,
substituted by substituents selected from the group consisting of:
  i. p-nitro,
  ii. halo, and
  iii. lower alkoxy containing from one to five carbon atoms, (e)

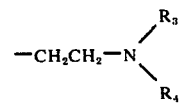

wherein
R₃ and R₄ are each independently selected from the group consisting of:
i. hydrogen,
ii. alkyl of 2 to 18 carbon atoms,
iii. substituted phenyl substituted by the substituents selected from the group consisting of:
a. p-nitro,
b. halo, and
c. lower alkoxy containing from one to five carbon atoms,
iv. benzyl,
v. lower-alkoxy carbonyl, and
vi. 2-hydroxy-lower alkyl containing from one to five carbon atoms, and (f) 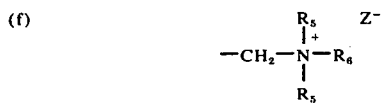

wherein
$R_5$ is lower alkyl;
$R_6$ is selected from the group consisting of:
i. alkyl of 3 to 8 carbon atoms,
ii. 2-hydroxy lower alkyl containing from one to five carbon atoms, and
$Z^-$ is selected from the group consisting of halide, nitrite, nitrate, diacid phosphate, sulfate and alkylsulfate.

2. The method of claim 1, wherein $R_1$ is methyl.
3. The method of claim 1, wherein $R_2$ is methyl.
4. The method of claim 1, wherein $R_2$ is 2-hydroxyalkyl of 3 to 18 carbon atoms.
5. The method of claim 1, wherein $R_1$ and $R_2$ are methyl.
6. The method of claim 1, wherein $R_1$ is a straight chain lower alkyl.
7. The method of claim 1, wherein $R_2$ is 2-hydroxy-n-propyl.
8. The method of claim 1, wherein $R_2$ is 2-hydroxy-n-octyl.
9. The method of claim 1, wherein $R_2$ is 2-hydroxy-n-octadecyl.
10. The method of claim 1, wherein $R_1$ is methyl and $R_2$ is 2-hydroxy-n-propyl.
11. The method of claim 1, wherein $R_1$ is methyl and $R_2$ is 2-hydroxy-n-octyl.
12. The method of claim 1, wherein $R_1$ is methyl and $R_2$ is 2-hydroxy-n-octadecyl.
13. The method of claim 1, wherein A is isopropyl.
14. The method of claim 1, wherein A is n-tridecyl.
15. The method of claim 1, wherein A is 2-hydroxyethyl.
16. The method of claim 1, wherein A is 2-allyl.
17. The method of claim 1, wherein A is p-nitro phenyl.
18. The method of claim 1, wherein A is o-chlorophenyl.
19. The method of claim 1, wherein A is p-methoxyphenyl.
20. The method of claim 1, wherein $R_3$ is a straight chain alkyl.
21. The method of claim 1, wherein $R_3$ is ethyl.
22. The method of claim 1, wherein $R_3$ is butyl.
23. The method of claim 1, wherein $R_3$ is dedecyl.
24. The method of claim 1, wherein $R_3$ is hexadecyl.
25. The method of claim 1, wherein $R_3$ is octadecyl.
26. The method of claim 1, wherein $R_4$ is hydrogen.
27. The method of claim 1, wherein $R_4$ is ethyl.
28. The method of claim 1, wherein $R_4$ is methoxy carbonyl.
29. The method of claim 1, wherein $R_4$ is 2-hydroxypropyl.
30. The method of claim 1, wherein $R_3$ is benzyl.
31. The method of claim 1, wherein $R_3$ is m-chlorophenyl.
32. The method of claim 1, wherein $R_5$ is methyl.
33. The method of claim 1, wherein $R_6$ is a straight chain alkyl.
34. The method of claim 1, wherein $R_6$ is n-octyl.
35. The method of claim 1, wherein $R_6$ is 2-hydroxyethyl.
36. The method of claim 1, wherein $Z^-$ is a chloride ion.
37. The method of claim 1, wherein the compound is 1,1-dimethyl-1-(2-hydroxypropyl)-2-isobutyryl ammonium imine.
38. The method of claim 1, wherein the compound is 1,1-dimethyl-1(2-hydroxypropyl)-2-tetradecanoyl ammonium imine.
39. The method of claim 1, wherein the compound is 1,1-dimethyl-1-(2-hydroxyoctadecyl)-2-(3-hydroxypropionyl) ammonium imine.
40. The method of claim 1, wherein the compound is 1,1-dimethyl-1-(2-hydroxyoctyl)-2-methacryloyl ammonium imine.
41. The method of claim 1, wherein the compound is 2-(4-nitrobenzoyl)-1,1,1-trimethyl ammonium imine.
42. The method of claim 1, wherein the compound is 2-(2-chlorobenzoyl)-1,1-dimethyl-1-(2-hydroxypropyl) ammonium imine.
43. The method of claim 1, wherein the compound is 1,1-dimethyl-1-(2-hydroxypropyl)-2-(4-methoxybenzoyl) ammonium imine.
44. The method of claim 1, wherein the compound is 1,1-dimethyl-1-(2-hydroxypropyl)-2-(3-octadecylaminopropionyl) ammonium imine.
45. The method of claim 1, wherein the compound is 1,1-dimethyl-1-(2-hydroxypropyl)-2-{3-[N-(2-hydroxypropyl-N-octadecylamino]propionyl} ammonium imine.
46. The method of claim 1, wherein the compound is 2-[3-(3-chloroaniline)propionyl]-1,1-dimethyl-1-(2-hydroxypropyl) ammonium imine.
47. The method of claim 1, wherein the compound is 2-[(3-benzylamino)propionyl]-1,1-dimethyl-1-(2-hydroxypropyl) ammonium imine.
48. The method of claim 1, wherein the compound is 2-(3-diethylaminopropionyl)-1,1,1-trimethyl ammonium imine.
49. The method of claim 1, wherein the compound is 2-[3-(n-butyl-N-methoxycarbonyl-amino)propionyl]-1,1-dimethyl-1-(2-hydroxypropyl) ammonium imine.
50. The method of claim 1, wherein the compound is 1,1-dimethyl-2{3-[N-dodecyl-N-(2-hydroxypropyl)amino]propionyl}1-(2-hydroxypropyl) ammonium imine.
51. The method of claim 1, wherein the compound is 1,1-dimethyl-2-{3-[N-hexadecyl-N-(2-hydroxypropyl)amino]propionyl}-1-(2-hydroxypropyl) ammonium imine.
52. The method of claim 1, wherein the compound is 1,1-dimethyl-2-(2-dimethyl octylammonioacetyl)-1-(2-hydroxypropyl) ammonium imine chloride.

53. The method of claim 1, wherein the compound is 1,1-dimethyl-2-(dimethyl-2-hydroxyethyl ammonioacetyl)-1-(2-hydroxypropyl) ammonium imine chloride.

54. The method of claim 1, wherein the compound is applied at a rate of from about 0.05 to about 50 pounds per acre.

55. The method of claim 1, wherein the compound is applied at a rate of from about 0.25 to about 5 pounds per acre.

56. The method of claim 1, wherein the compound is applied in the form of a solution containing from about 10 to about 10,000 ppm of the compound.

57. The method of claim 1, wherein the compound is applied in the form of a solution containing from about 100 to about 5,000 ppm of the compound.

58. The method of claim 1, wherein the plant being treated is squash.

59. The method of claim 50, wherein the plant being treated is bean; and the compound is applied at a rate of 0.8 lb/A.

60. The method of claim 50, wherein the plant being treated is beans.

61. The method of claim 50, wherein the plant being treated is corn.

62. The method of claim 50, wherein the plant being treated is tomatoes.

63. The method of claim 50, wherein the plant being treated is peaches.

* * * * *